United States Patent
Grobys et al.

(10) Patent No.: US 7,067,558 B2
(45) Date of Patent: Jun. 27, 2006

(54) PROCESS FOR THE PRODUCTION OF CARBON MONOXIDE AND METHANOL

(75) Inventors: Mauricio Grobys, The Woodlands, TX (US); Hermann Göhna, Bad Soden (DE); Thomas Wurzel, Frankfurt am Main (DE)

(73) Assignee: Lurgi AG, Frankfurt (DE)

( * ) Notice: Subject to any disclaimer, the term of this patent is extended or adjusted under 35 U.S.C. 154(b) by 0 days.

(21) Appl. No.: 10/396,235

(22) Filed: Mar. 25, 2003

(65) Prior Publication Data

US 2004/0034110 A1   Feb. 19, 2004

(30) Foreign Application Priority Data

Mar. 27, 2002   (DE) ................. 102 14 003

(51) Int. Cl.
*C07C 27/00*   (2006.01)
(52) U.S. Cl. ............... 518/700; 518/702; 518/703; 518/704; 518/705

(58) Field of Classification Search ........... 518/700, 518/702, 703, 704, 705
See application file for complete search history.

(56) References Cited

U.S. PATENT DOCUMENTS 4,927,857 A * 5/1990 McShea et al. ............ 518/703
6,232,352 B1 * 5/2001 Vidalin ...................... 518/700

FOREIGN PATENT DOCUMENTS

DE         2 056824        5/1971
EP         0 533 231 A1    3/1993

* cited by examiner

*Primary Examiner*—J. Parsa
(74) *Attorney, Agent, or Firm*—Norris McLaughlin & Marcus PA

(57) ABSTRACT

A process for the production of methanol from liquid or gaseous starting materials, in which the emission of carbon dioxide is reduced or completely eliminated.

8 Claims, 1 Drawing Sheet

PROCESS FOR THE PRODUCTION OF CARBON MONOXIDE AND METHANOL

The invention relates to a process for the production of methanol from liquid or gaseous starting materials in which a synthesis gas having a gas composition with a stoichiometry number SN of <2 is produced from these starting materials by catalytic or non-catalytic partial oxidation with addition of oxygen and steam, and this synthesis gas is enriched with hydrogen and/or the carbon-containing components carbon monoxide and/or carbon dioxide are removed in order to achieve the stoichiometry number of from 2.0 to 2.2 which is necessary for the synthesis of methanol.

BACKGROUND OF THE INVENTION

Worldwide initiatives for climate protection and for reducing the global emission of greenhouse gases make it necessary to design industrial plants which have the lowest possible emission of carbon dioxide.

The general state of the art (for example DE-C-2056824, EP-A-0533231) is to use various processes to set the stoichiometry number necessary for the synthesis of methanol. U.S. Pat. No. 6,232,352 describes a process in which carbon monoxide and methanol are provided for the production of acetic acid. The synthesis gas here is produced by steam reforming.

Based on this prior art, the invention has the object of developing an inexpensive process for the production of methanol in which the emission of carbon dioxide is reduced or even completely eliminated.

SUMMARY OF THE INVENTION

In accordance with the invention, the object is achieved in the process mentioned at the outset in that liquid or gaseous starting materials, oxygen and steam are fed to an autothermally operated reactor for the production of synthesis gas, a sub-stream of the synthesis gas is branched off, and the carbon dioxide present therein is removed by carbon dioxide separation, in that all or some of this carbon dioxide is fed back into the synthesis gas production, in that the carbon dioxide-free gas removed from the carbon dioxide separation is subjected to separation, producing carbon monoxide, and all or some of the hydrogen separated off is fed back to the synthesis gas, and in that the hydrogen enriched synthesis gas is converted into methanol and purge gas in the synthesis of methanol.

DETAILED DESCRIPTION OF THE INVENTION

Compared with conventional processes, this process enables the operation of a plant for the production of methanol which produces no or only low emission of carbon dioxide. Some of the carbon dioxide fed back into the synthesis gas production is converted into carbon monoxide in the reactor. The hydrogen separated off is used to set the stoichiometry necessary for methanol production, and pure carbon monoxide can be isolated as product. In the case of recycling of all of the carbon dioxide and purge gas, it is possible to produce methanol without emission of carbon dioxide. If only some of the carbon dioxide and purge gas is recycled, the emission of carbon dioxide is nevertheless significantly reduced.

The plant configuration enables methanol to be produced with supply of external carbon dioxide with the plant consumption of carbon dioxide being greater than the emission of carbon dioxide.

The carbon monoxide can be separated off by means of cryogenic separation or through membranes.

The carbon dioxide emission by the preheater can be reduced by using some of the hydrogen formed from the gas separation for heating the preheater from below.

The reduction or elimination of carbon dioxide-containing offgases from the preheater is likewise achieved by separating the purge gas from the synthesis of methanol into a hydrogen-rich fraction and a carbon-rich fraction by means of gas separation, and using the hydrogen-rich fraction for heating the preheater from below. The carbon-rich fraction is fed back upstream of the preheater for partial oxidation.

The carbon monoxide formed from the gas separation downstream of the carbon dioxide separation can be further processed directly with some of the methanol. A plant for the production of acetic acid is preferred here.

Catalytic partial oxidation operating without indirect heating is known and is described, for example, in Ullmann's Encyclopaedia of Industrial Chemistry, 5th Edition, Volume A12, pages 202 to 204.

The liquid or gaseous starting materials, the steam and the oxidant are preferably fed preheated to the reactor. Starting materials which can be used are preferably natural gas, but also liquid gas or refinery gas. Industrially pure oxygen is usually fed to the reactor burner in order to keep the content of inert gas in the crude synthesis gas as low as possible. However, it is optionally also possible to process an oxygen/air mixture. Steam is usually supplied in the range from 0.2 to 3.0 mol, based on the molar carbon content of the natural gas.

Processes which are known per se are suitable for the methanol synthesis, in particular those which operate with a water-cooled tubular reactor or with an adiabatically operated fixed-bed reactor or a combination of a water-cooled reactor and a gas-cooled reactor.

A further improvement is achieved by employing a prereactor operating with an active nickel catalyst between the stages of the preheater, and converting higher hydrocarbons in the natural gas, such as, for example, ethane or propane, into methane, carbon monoxide and hydrogen. This prereacted gas can be preheated to any desired extent without cracking reactions.

BRIEF DESCRIPTION OF THE DRAWINGS

Possible designs of the process are explained by way of example with the aid of the drawing. The drawing shows a flow chart of the process.

In a fired preheater (1), natural gas is supplied and preheated via line (2) and steam via line (3), and fed to a reactor (5) for partial oxidation via line (4). Oxygen is recovered from air via line (6) by a separation (7) and likewise fed to the reactor (5) via line (8). In this reactor (5), a synthesis gas which essentially consists of $H_2$, CO and $CO_2$ and has a stoichiometry number SN of <2 ($SN=(H_2-CO_2)/(CO+CO_2)$ mol/mol) is produced by partial oxidation. This gas is withdrawn from the reactor (5) via line (9). After cooling, the unreacted, condensed steam is withdrawn via line (30). Some of the synthesis gas is branched off via line (10), and the $CO_2$ present therein is removed by a separation (11), usually a gas wash. The $CO_2$ from the separation (11) is fed via line (12) to a compressor (13) and then back to the synthesis gas reactor (5). At this point, $CO_2$ can also be supplied from external sources (14).

Figure 1:
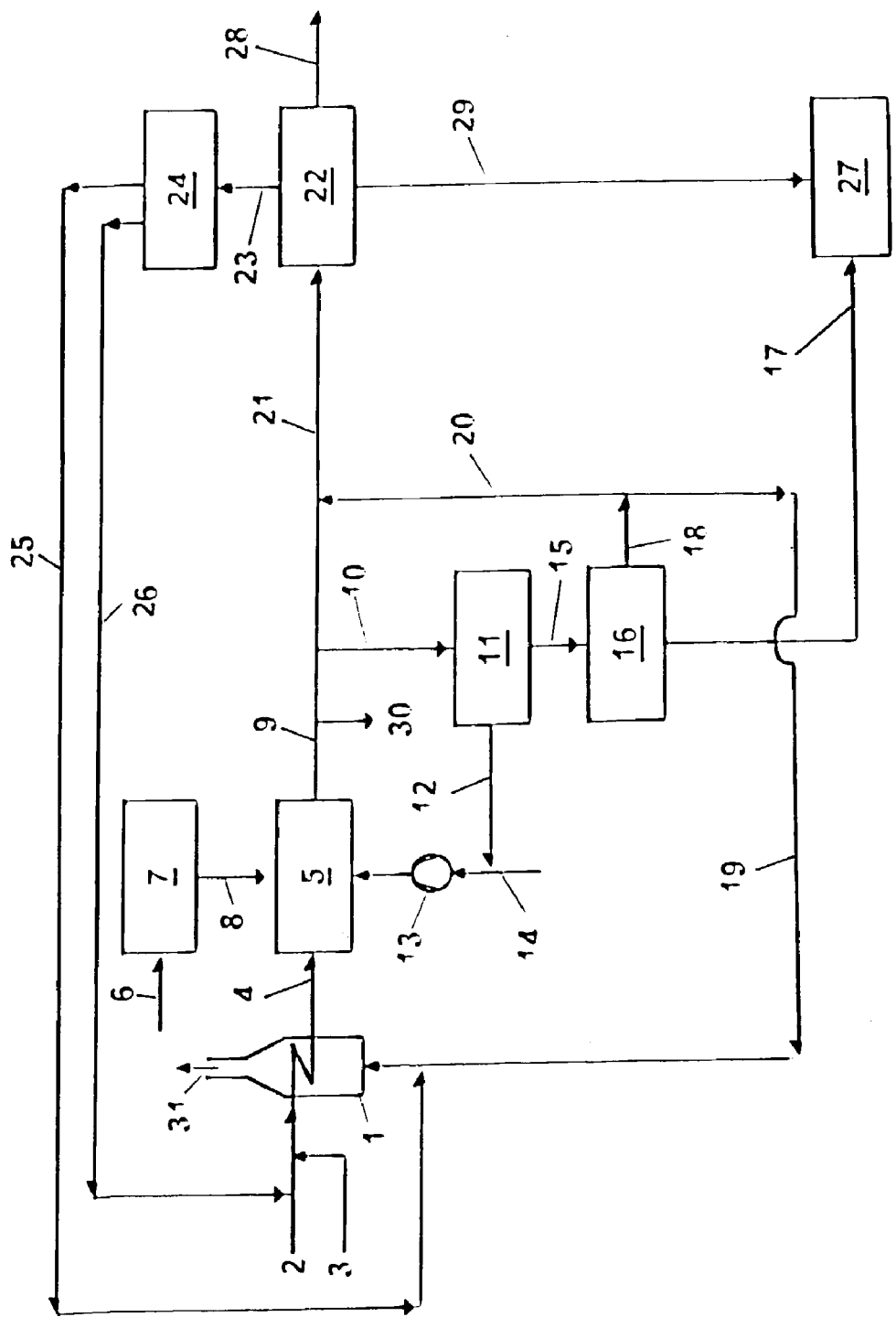

The $CO_2$-free gas from the gas wash (11) is fed to a cryogenic separation (16) via line (15). The carbon monoxide produced therein typically has a purity of >98% by volume of CO. Lower purities are possible depending on the subsequent CO use. The hydrogen-rich gas (18) produced in the low-temperature distillation is split over lines (19) and (20). All or some of the hydrogen-rich gas (18) can be fed back to the main synthesis-gas stream (9) via line (20). From the point of introduction of the hydrogen-rich gas via line (20) into the main synthesis-gas stream (9), the gas composition with the stoichiometry number of from 2.0 to 2.2 which is necessary for the methanol synthesis is achieved. This synthesis gas necessary for the production of methanol is subsequently converted into methanol in the methanol synthesis (22) via line (21). In the case where only a sub-stream (20) of the hydrogen-rich gas is fed back to the main synthesis-gas stream (9), the remaining hydrogen-rich gas fraction is taken via line (19) to heat the preheater (1) from below.

The purge gas (23) from the methanol synthesis (22) is separated in the gas separation (24) into a hydrogen-rich fraction (25) and a carbon-rich fraction (26). The hydrogen-rich fraction (25) is burned in the preheater (1) as heating medium, and the carbon-rich fraction (26) is fed to the preheater (1) on the process side. Process products are methanol (28) and carbon monoxide (17). Some of the methanol (29) and some of the carbon monoxide (17) can be further processed directly, for example in a downstream acetic acid plant (27). Acetic acid is nowadays usually produced by catalytic carbonylation of methanol, such as, for example, in the BP Chemicals or Celanese processes. Additional areas of use for carbon monoxide are conceivable.

The only emission source for carbon dioxide is the flue gas (31) from the preheater (1). Not shown is the optional use of a pre-reactor employed between the stages of the preheater (1).

EXAMPLE

The following example, which has been partially calculated, has the aim of producing 2500 day-tonnes of methanol and 586 day-tonnes of CO (98.8%). The synthesis gas is produced in a catalytic partial oxidation. An optional pre-reactor which converts the higher hydrocarbons in the natural gas into methane, carbon dioxide and hydrogen is installed upstream of the synthesis gas reactor (5). This pre-reacted gas can be preheated to any desired extent without cracking reactions.

The carbon dioxide-free gas stream (15) is fractionated in a low-temperature fractionation (16). The purge gas (23) in the methanol synthesis (22) is fractionated in a membrane unit (24). The compressors and all essential fans and pumps are driven by means of steam turbines. Both the turbine drive steam and the process steam are obtained from waste heat from the process. The only outlet for $CO_2$ is the flue gas (31) from the preheater (1).

A plant is used which substantially corresponds to the drawing. In the preheater (1), 4444 kmol/h of natural gas and 6885 kmol/h of steam are preheated to 500° C. in a first stage of the preheater. After reaction of the preheated starting-gas stream in the pre-reactor, residual gas from line (26) and 528 kmol/h of $CO_2$ from line (12) are mixed with the exit gas and preheated to 600° C. in the preheater (1).

Besides methane, the natural gas comprises 3.91 mol % of $C_2H_8$, 0.03 mol % of $C_3H_8$, 0.59 mol % of $CO_2$ and 0.08 mol % of $N_2$. In addition to the exit gas from the pre-reactor, 2556 kmol/h of oxygen (purity 99.5 mol %) are fed to the catalytic partial oxidation (5).

Further details can be taken from the following table, with the components of the respective mixture being indicated in mol % and kmol/h for various lines.

|  | Line | | | | | | | | | |
|---|---|---|---|---|---|---|---|---|---|---|
|  | 9 | | 10 | | 19 | | 20 | | 21 | |
|  | mol % | kmol/h | mol % | kmol/h | mol % | kmol/h | mol % | kmol/h | mol % | kmol/h |
| $CO_2$ | 7.67 | 1662 | 10.87 | 528 | — | — | — | — | 8.87 | 1125 |
| CO | 16.90 | 3663 | 24.09 | 1170 | 2.91 | 26 | 2.92 | 68 | 20.18 | 2560 |
| $H_2$ | 43.94 | 9527 | 62.64 | 3042 | 94.30 | 843 | 94.30 | 2199 | 68.45 | 8683 |
| $CH_4$ | 1.25 | 272 | 1.79 | 87 | 2.68 | 24 | 2.70 | 63 | 1.95 | 248 |
| $N_2$ and Ar | 0.24 | 52 | 0.35 | 17 | 0.11 | 1 | 0.09 | 2 | 0.30 | 38 |
| $CH_3OH$ | — | — | — | — | — | — | — | — | — | — |
| $H_2O$ | 30.00 | 6504 | 0.25 | 12 | — | — | — | — | 0.25 | 32 |
| Total amount (kmol/h) | | 21680 | | 4856 | | 894 | | 2332 | | 12686 |
| Temperature (° C.) | | 960 | | 40 | | 40 | | 40 | | 40 |
| Pressure (bar a) | | 34 | | 31 | | 29 | | 29 | | 29 |

The stoichiometry number S is S = 1.48 in the crude synthesis gas in line (9) and is S = 2.05 in the gas in line (21).

|  | Line | | | | | | | |
|---|---|---|---|---|---|---|---|---|
|  | 23 | | 25 | | 26 | | 31 | |
|  | mol % | kmol/h | mol % | kmol/h | mol % | kmol/h | mol % | kmol/h |
| $CO_2$ | 11.10 | 195 | 2.44 | 25 | 23.06 | 169 | 1.52 | 94 |
| CO | 3.64 | 64 | 0.20 | 2 | 6.59 | 63 | — | — |
| $H_2$ | 69.65 | 1223 | 95.50 | 978 | 33.42 | 245 | — | — |
| $CH_4$ | 12.98 | 228 | 1.56 | 16 | 28.92 | 212 | — | — |
| $N_2$ and Ar | 2.05 | 36 | 0.10 | 1 | 4.91 | 36 | 66.46 | 4118 |
| $CH_3OH$ | 0.51 | 9 | 0.20 | 2 | 0.95 | 7 | — | — |
| $H_2O$ | 0.06 | 1 | 0.01 | 0.1 | 0.14 | 1 | 30.42 | 1885 |
| $O_2$ | — | — | — | — | — | — | 1.60 | 99 |
| Total amount (kmol/h) |  | 1756 |  | 1024 |  | 733 |  | 6196 |
| Temperature (° C.) |  | 40 |  | 40 |  | 40 |  | 190 |
| Pressure (bar a) |  | 78 |  | 5 |  | 77 |  | 1 |

We claim:

1. A Process for the production of methanol from liquid or gaseous starting materials in which a synthesis gas (9) is produced from these starting materials by catalytic or non-catalytic partial oxidation with addition of oxygen and steam, wherein a sub-stream (10) of the synthesis gas is branched off, and the carbon dioxide present therein is removed by carbon dioxide separation (11), and all or some of this carbon dioxide is fed back into the synthesis gas production (5), the carbon dioxide-free gas removed from the carbon dioxide separation (11) is subjected to separation (16), producing carbon monoxide, and all or some of the hydrogen separated off is fed back to the synthesis gas, and in that the hydrogen-enriched synthesis gas is converted into methanol and purge gas in the synthesis (22) of methanol.

2. Process according to claim 1, wherin the carbon dioxide-free gas removed from the carbon dioxide separation (11) is separated into carbon monoxide and hydrogen by cryogenic separation.

3. Process according to claim 1, wherein the carbon dioxide-free gas removed from the carbon dioxide wash (11) is separated into carbon monoxide and hydrogen by membranes.

4. Process according to claim 1, wherein some of the carbon monoxide from the gas separation (16) is processed further with some of the methanol in a plant (27) to produce another product.

5. Process according to claim 1, wherein some of the hydrogen formed from the gas separation (16) is used for heating the preheater (1) from below.

6. Process according to claim 1, wherin the purge gas (23) in the methanol synthesis (22) is separated into a hydrogen-rich fraction (25) and a carbon-rich fraction (26), and the hydrogen-rich fraction (25) is used for heating the preheater (1) from below and the carbon-rich fraction (26) is recycled back for partial oxidation step.

7. Process according to claim 1, wherein a pre-reactor filled with highly active nickel catalyst is installed upstream of the partial catalytic oxidation.

8. Process according to claim 1, wherein carbon dioxide from external sources is fed to the reactor (5).

* * * * *

UNITED STATES PATENT AND TRADEMARK OFFICE
CERTIFICATE OF CORRECTION

PATENT NO. : 7,067,558 B2
APPLICATION NO. : 10/396235
DATED : June 27, 2006
INVENTOR(S) : Grobys et al.

It is certified that error appears in the above-identified patent and that said Letters Patent is hereby corrected as shown below:

Column 5, Line 10, "3.64  64  0.20  2  6.59  63" should read -- 3.64  64  0.20  2  8.59  63 --

Signed and Sealed this

First Day of April, 2008

JON W. DUDAS
*Director of the United States Patent and Trademark Office*